US010920202B1

(12) United States Patent
Zhu et al.

(10) Patent No.: US 10,920,202 B1
(45) Date of Patent: Feb. 16, 2021

(54) THERMOLABILE SERRATIA MARCESCENS NUCLEASE

(71) Applicant: AbClonal Science, Inc., Woburn, MA (US)

(72) Inventors: Zhenyu Zhu, Lynnfield, MA (US); Dapeng Sun, Lexington, MA (US); Michaela Shottes, Methuen, MA (US)

(73) Assignee: AbClonal Science, Inc., Woburn, MA (US)

( * ) Notice: Subject to any disclaimer, the term of this patent is extended or adjusted under 35 U.S.C. 154(b) by 0 days.

(21) Appl. No.: 16/998,705

(22) Filed: Aug. 20, 2020

(51) Int. Cl.
 *C12N 9/22* (2006.01)
 *C12N 15/10* (2006.01)
 *C12N 9/16* (2006.01)

(52) U.S. Cl.
 CPC ........ *C12N 9/16* (2013.01); *C12Y 301/30002* (2013.01)

(58) Field of Classification Search
 CPC .................................. C12N 9/22; C12P 21/02
 See application file for complete search history.

(56) References Cited

U.S. PATENT DOCUMENTS 9,796,994 B2 * 10/2017 Greiner-Stoeffele ... C12P 21/02

FOREIGN PATENT DOCUMENTS

WO 125804 * 6/2019

OTHER PUBLICATIONS

Company literature about Benzonase.
Company literature about Turbonuclease.

* cited by examiner

*Primary Examiner* — Maryam Monshipouri
(74) *Attorney, Agent, or Firm* — Eric P. Mirabel

(57) ABSTRACT

Disclosed is an engineered thermolabile mutant of *Serratia Marcescens* Nuclease. In the same buffer as used for optimal enzyme activity, after 60° C. for 20 min, while the wild type retained 12.5% activity, the thermolabile mutant R146D/D156R/D229R/D245R (SEQ ID NO: 12, without the first 21 amino acids, which are a signal peptide) retained only 0.39% activity. Heat inactivation of the mutant, when it is used for protein purification, can be used after a period when substantial DNA in a protein has been degraded, but before unwanted degradation takes place.

5 Claims, 1 Drawing Sheet

Specification includes a Sequence Listing.

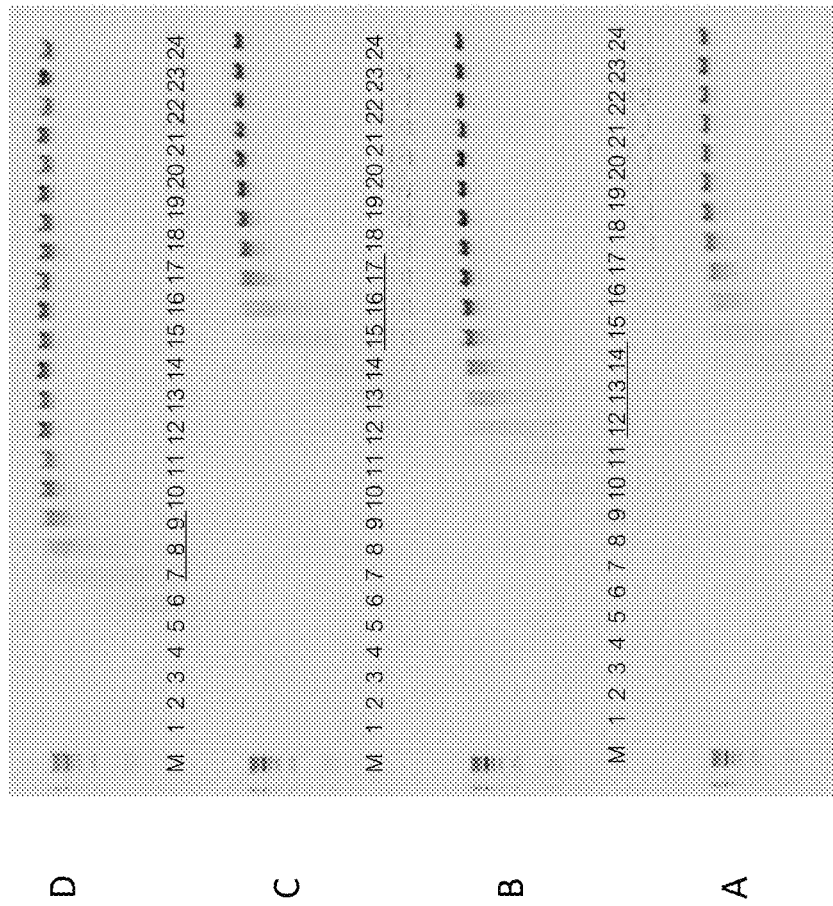

SEQUENCE LISTING

<160> NUMBER OF SEQ ID NOS: 12

<210> SEQ ID NO 1
<211> LENGTH: 798
<212> TYPE: DNA
<213> ORGANISM: Serratia marcescens

<400> SEQUENCE: 1

```
atgcgcttta caacaagat gctggcgctg ccgctttac tgttcgcggc acaggcttcg      60
gcggacaccc tggaaagtat cgacaattgt gcggtcggtt gcccgactgg tggctcgagc   120
aatgtgtcga tcgttcgtca tgcttatacc cttaataata actcgaccac gaaattcgct   180
aactgggtag catatcacat tactaaggac actccggcca gcggtaagac gcgcaactgg   240
aagaccgatc cggcgctcaa tccggcagac accttagcac cggctgatta taccggtgca   300
aacgctgcgc tgaaggtgga tcgtggtcac caggcgccgt tggcatctct ggctggtgta   360
agcgactggg aaagccttaa ctatctcagc aacatcaccc cgcaaaagtc cgacctgaac   420
cagggagcct gggcacgtct ggaggaccaa gagcgtaagc tgattgatcg gccgacatt    480
tcatcggtct acaccgtgac gggtccgctg tacgaacgtg atatgggcaa attaccgggt   540
acccaaaaag cacacacaat cccttcagcg tattggaaag tcatctttat taataactca   600
ccagcggtta atcactatgc tgcatttctc tttgatcaaa atacgccgaa agggggcagat  660
ttctgtcaat ttcgcgtgac cgttgatgag atcgaaaagc ggactggcct cattatttgg   720
gccggcctgc cggatgacgt gcaggcctcc ctgaagagta aaccgggcgt tctgccggaa   780
ttaatgggct gtaagaac                                                 798
```

<210> SEQ ID NO 2
<211> LENGTH: 266
<212> TYPE: PRT
<213> ORGANISM: Serratia marcescens

<400> SEQUENCE: 2

```
Met Arg Phe Asn Asn Lys Met Leu Ala Leu Ala Ala Leu Leu Phe Ala
1               5                   10                  15

Ala Gln Ala Ser Ala Asp Thr Leu Glu Ser Ile Asp Asn Cys Ala Val
            20                  25                  30

Gly Cys Pro Thr Gly Gly Ser Ser Asn Val Ser Ile Val Arg His Ala
        35                  40                  45

Tyr Thr Leu Asn Asn Asn Ser Thr Thr Lys Phe Ala Asn Trp Val Ala
    50                  55                  60

Tyr His Ile Thr Lys Asp Thr Pro Ala Ser Gly Lys Thr Arg Asn Trp
65                  70                  75                  80

Lys Thr Asp Pro Ala Leu Asn Pro Ala Asp Thr Leu Ala Pro Ala Asp
                85                  90                  95

Tyr Thr Gly Ala Asn Ala Ala Leu Lys Val Asp Arg Gly His Gln Ala
            100                 105                 110

Pro Leu Ala Ser Leu Ala Gly Val Ser Asp Trp Glu Ser Leu Asn Tyr
        115                 120                 125

Leu Ser Asn Ile Thr Pro Gln Lys Ser Asp Leu Asn Gln Gly Ala Trp
    130                 135                 140

Ala Arg Leu Glu Asp Gln Glu Arg Lys Leu Ile Asp Arg Ala Asp Ile
145                 150                 155                 160

Ser Ser Val Tyr Thr Val Thr Gly Pro Leu Tyr Glu Arg Asp Met Gly
                165                 170                 175

Lys Leu Pro Gly Thr Gln Lys Ala His Thr Ile Pro Ser Ala Tyr Trp
            180                 185                 190

Lys Val Ile Phe Ile Asn Asn Ser Pro Ala Val Asn His Tyr Ala Ala
        195                 200                 205

Phe Leu Phe Asp Gln Asn Thr Pro Lys Gly Ala Asp Phe Cys Gln Phe
```

```
              210                 215                 220
Arg Val Thr Val Asp Glu Ile Glu Lys Arg Thr Gly Leu Ile Ile Trp
225                 230                 235                 240

Ala Gly Leu Pro Asp Asp Val Gln Ala Ser Leu Lys Ser Lys Pro Gly
                245                 250                 255

Val Leu Pro Glu Leu Met Gly Cys Lys Asn
            260                 265
```

<210> SEQ ID NO 3
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgcgcttta acaacaagat gctggcgctg ccgctttac tgttcgcggc acaggcttcg      60
gcggacaccc tggaaagtat cgacaattgt gcggtcggtt gcccgactgg tggctcgagc    120
aatgtgtcga tcgttcgtca tgcttatacc cttaataata actcgaccac gaaattcgct    180
aactgggtag catatcacat tactaaggac actccggcca gcggtaagac gcgcaactgg    240
aagaccgatc cggcgctcaa tccggcagac accttagcac cggctgatta ccggtgca     300 aacgctgcgc tgaaggtgga tcgtggtcac caggcgccgt ggcatctct ggctggtgta   360 agcgactggg aaagccttaa ctatctcagc aacatcaccc cgcaaaagtc cgacctgaac    420
cagggagcct gggcagacct ggaggaccaa gagcgtaagc tgattgatcg gccgacatt    480 tcatcggtct acaccgtgac gggtccgctg tacgaacgtg atatgggcaa attaccgggt    540
acccaaaaag cacacacaat cccttcagcg tattggaaag tcatctttat taataactca    600
ccagcggtta atcactatgc tgcatttctc tttgatcaaa atacgccgaa aggggcagat    660
ttctgtcaat ttcgcgtgac cgttgatgag atcgaaaagc ggactggcct cattatttgg    720
gccggcctgc cggatgacgt gcaggcctcc ctgaagagta aaccgggcgt tctgccggaa    780
ttaatgggct gtaagaac                                                   798
```

<210> SEQ ID NO 4
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Arg Phe Asn Asn Lys Met Leu Ala Leu Ala Leu Leu Phe Ala
1                 5                  10                  15

Ala Gln Ala Ser Ala Asp Thr Leu Glu Ser Ile Asp Asn Cys Ala Val
                20                  25                  30

Gly Cys Pro Thr Gly Gly Ser Ser Asn Val Ser Ile Val Arg His Ala
            35                  40                  45

Tyr Thr Leu Asn Asn Asn Ser Thr Thr Lys Phe Ala Asn Trp Val Ala
        50                  55                  60

Tyr His Ile Thr Lys Asp Thr Pro Ala Ser Gly Lys Thr Arg Asn Trp
65                  70                  75                  80

Lys Thr Asp Pro Ala Leu Asn Pro Ala Asp Thr Leu Ala Pro Ala Asp
                85                  90                  95
```

Tyr Thr Gly Ala Asn Ala Ala Leu Lys Val Asp Arg Gly His Gln Ala
            100                 105                 110

Pro Leu Ala Ser Leu Ala Gly Val Ser Asp Trp Glu Ser Leu Asn Tyr
        115                 120                 125

Leu Ser Asn Ile Thr Pro Gln Lys Ser Asp Leu Asn Gln Gly Ala Trp
    130                 135                 140

Ala Asp Leu Glu Asp Gln Glu Arg Lys Leu Ile Asp Arg Ala Asp Ile
145                 150                 155                 160

Ser Ser Val Tyr Thr Val Thr Gly Pro Leu Tyr Glu Arg Asp Met Gly
                165                 170                 175

Lys Leu Pro Gly Thr Gln Lys Ala His Thr Ile Pro Ser Ala Tyr Trp
            180                 185                 190

Lys Val Ile Phe Ile Asn Asn Ser Pro Ala Val Asn His Tyr Ala Ala
        195                 200                 205

Phe Leu Phe Asp Gln Asn Thr Pro Lys Gly Ala Asp Phe Cys Gln Phe
    210                 215                 220

Arg Val Thr Val Asp Glu Ile Glu Lys Arg Thr Gly Leu Ile Ile Trp
225                 230                 235                 240

Ala Gly Leu Pro Asp Asp Val Gln Ala Ser Leu Lys Ser Lys Pro Gly
                245                 250                 255

Val Leu Pro Glu Leu Met Gly Cys Lys Asn
            260                 265

<210> SEQ ID NO 5
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgcgcttta acaacaagat gctggcgctg gccgctttac tgttcgcggc acaggcttcg    60
gcggacaccc tggaaagtat cgacaattgt gcggtcggtt gcccgactgg tggctcgagc    120
aatgtgtcga tcgttcgtca tgcttatacc cttaataata actcgaccac gaaattcgct    180
aactgggtag catatcacat tactaaggac actccggcca gcggtaagac gcgcaactgg    240
aagaccgatc cggcgctcaa tccggcagac accttagcac cggctgatta taccggtgca    300
aacgctgcgc tgaaggtgga tcgtggtcac caggcgccgt ggcatctctg gctggtgta    360 agcgactggg aaagccttaa ctatctcagc aacatcaccc cgcaaaagtc cgacctgaac    420
cagggagcct gggcacgtct ggaggaccaa gagcgtaagc tgattcgtcg ggccgacatt    480
tcatcggtct acaccgtgac gggtccgctg tacgaacgtg atatgggcaa attaccgggt    540
acccaaaaag cacacacaat cccttcagcg tattggaaag tcatctttat taataactca    600
ccagcggtta atcactatgc tgcatttctc tttgatcaaa atacgccgaa aggggcagat    660
ttctgtcaat ttcgcgtgac cgttgatgag atcgaaaagc ggactggcct cattatttgg    720
gccggcctgc cggatgacgt gcaggcctcc ctgaagagta aaccgggcgt tctgccggaa    780
ttaatgggct gtaagaac                                                  798

<210> SEQ ID NO 6
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Met Arg Phe Asn Asn Lys Met Leu Ala Leu Ala Ala Leu Leu Phe Ala
1               5                   10                  15

Ala Gln Ala Ser Ala Asp Thr Leu Glu Ser Ile Asp Asn Cys Ala Val
            20                  25                  30

Gly Cys Pro Thr Gly Gly Ser Ser Asn Val Ser Ile Val Arg His Ala
        35                  40                  45

Tyr Thr Leu Asn Asn Asn Ser Thr Thr Lys Phe Ala Asn Trp Val Ala
    50                  55                  60

Tyr His Ile Thr Lys Asp Thr Pro Ala Ser Gly Lys Thr Arg Asn Trp
65                  70                  75                  80

Lys Thr Asp Pro Ala Leu Asn Pro Ala Asp Thr Leu Ala Pro Ala Asp
                85                  90                  95

Tyr Thr Gly Ala Asn Ala Ala Leu Lys Val Asp Arg Gly His Gln Ala
            100                 105                 110

Pro Leu Ala Ser Leu Ala Gly Val Ser Asp Trp Glu Ser Leu Asn Tyr
        115                 120                 125

Leu Ser Asn Ile Thr Pro Gln Lys Ser Asp Leu Asn Gln Gly Ala Trp
    130                 135                 140

Ala Arg Leu Glu Asp Gln Glu Arg Lys Leu Ile Arg Arg Ala Asp Ile
145                 150                 155                 160

Ser Ser Val Tyr Thr Val Thr Gly Pro Leu Tyr Glu Arg Asp Met Gly
                165                 170                 175

Lys Leu Pro Gly Thr Gln Lys Ala His Thr Ile Pro Ser Ala Tyr Trp
            180                 185                 190

Lys Val Ile Phe Ile Asn Asn Ser Pro Ala Val Asn His Tyr Ala Ala
        195                 200                 205

Phe Leu Phe Asp Gln Asn Thr Pro Lys Gly Ala Asp Phe Cys Gln Phe
    210                 215                 220

Arg Val Thr Val Asp Glu Ile Glu Lys Arg Thr Gly Leu Ile Ile Trp
225                 230                 235                 240

Ala Gly Leu Pro Asp Asp Val Gln Ala Ser Leu Lys Ser Lys Pro Gly
                245                 250                 255

Val Leu Pro Glu Leu Met Gly Cys Lys Asn
            260                 265

<210> SEQ ID NO 7
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgcgcttta caacaagat gctggcgctg gccgctttac tgttcgcggc acaggcttcg      60
gcggacaccc tggaaagtat cgacaattgt gcggtcggtt gcccgactgg tggctcgagc    120
aatgtgtcga tcgttcgtca tgcttatacc cttaataata actcgaccac gaaattcgct    180
aactgggtag catatcacat tactaaggac actccggcca gcggtaagac gcgcaactgg    240
aagaccgatc cggcgctcaa tccggcagac accttagcac cggctgatta taccggtgca    300
aacgctgcgc tgaaggtgga tcgtggtcac caggcgccgt tggcatctct ggctggtgta    360
agcgactggg aaagccttaa ctatctcagc aacatcaccc cgcaaaagtc cgacctgaac    420

```
cagggagcct gggcacgtct ggaggaccaa gagcgtaagc tgattgatcg ggccgacatt    480
tcatcggtct acaccgtgac gggtccgctg tacgaacgtg atatgggcaa attaccgggt    540
acccaaaaag cacacacaat cccttcagcg tattggaaag tcatctttat taataactca    600
ccagcggtta atcactatgc tgcatttctc tttgatcaaa atacgccgaa aggggcagat    660
ttctgtcaat ttcgcgtgac cgttcgtgag atcgaaaagc ggactggcct cattatttgg    720
gccggcctgc cggatgacgt gcaggcctcc ctgaagagta aaccgggcgt tctgccggaa    780
ttaatgggct gtaagaac                                                  798
```

```
<210> SEQ ID NO 8
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

Met Arg Phe Asn Asn Lys Met Leu Ala Leu Ala Ala Leu Leu Phe Ala
1               5                   10                  15

Ala Gln Ala Ser Ala Asp Thr Leu Glu Ser Ile Asp Asn Cys Ala Val
            20                  25                  30

Gly Cys Pro Thr Gly Gly Ser Ser Asn Val Ser Ile Val Arg His Ala
        35                  40                  45

Tyr Thr Leu Asn Asn Asn Ser Thr Thr Lys Phe Ala Asn Trp Val Ala
    50                  55                  60

Tyr His Ile Thr Lys Asp Thr Pro Ala Ser Gly Lys Thr Arg Asn Trp
65                  70                  75                  80

Lys Thr Asp Pro Ala Leu Asn Pro Ala Asp Thr Leu Ala Pro Ala Asp
                85                  90                  95

Tyr Thr Gly Ala Asn Ala Ala Leu Lys Val Asp Arg Gly His Gln Ala
            100                 105                 110

Pro Leu Ala Ser Leu Ala Gly Val Ser Asp Trp Glu Ser Leu Asn Tyr
        115                 120                 125

Leu Ser Asn Ile Thr Pro Gln Lys Ser Asp Leu Asn Gln Gly Ala Trp
    130                 135                 140

Ala Arg Leu Glu Asp Gln Glu Arg Lys Leu Ile Asp Arg Ala Asp Ile
145                 150                 155                 160

Ser Ser Val Tyr Thr Val Thr Gly Pro Leu Tyr Glu Arg Asp Met Gly
                165                 170                 175

Lys Leu Pro Gly Thr Gln Lys Ala His Thr Ile Pro Ser Ala Tyr Trp
            180                 185                 190

Lys Val Ile Phe Ile Asn Asn Ser Pro Ala Val Asn His Tyr Ala Ala
        195                 200                 205

Phe Leu Phe Asp Gln Asn Thr Pro Lys Gly Ala Asp Phe Cys Gln Phe
    210                 215                 220

Arg Val Thr Val Arg Glu Ile Glu Lys Arg Thr Gly Leu Ile Ile Trp
225                 230                 235                 240

Ala Gly Leu Pro Asp Asp Val Gln Ala Ser Leu Lys Ser Lys Pro Gly
                245                 250                 255

Val Leu Pro Glu Leu Met Gly Cys Lys Asn
            260                 265

```
<210> SEQ ID NO 9
```

<211> LENGTH: 798
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
atgcgcttta caacaagat gctggcgctg ccgctttac tgttcgcggc acaggcttcg      60
gcggacaccc tggaaagtat cgacaattgt gcggtcggtt gcccgactgg tggctcgagc   120
aatgtgtcga tcgttcgtca tgcttatacc cttaataata actcgaccac gaaattcgct   180
aactgggtag catatcacat tactaaggac actccggcca gcgtaagac gcgcaactgg    240
aagaccgatc cggcgctcaa tccggcagac accttagcac cggctgatta taccggtgca   300
aacgctgcgc tgaaggtgga tcgtggtcac caggcgccgt tggcatctct ggctggtgta   360
agcgactggg aaagccttaa ctatctcagc aacatcaccc cgcaaaagtc cgacctgaac   420
cagggagcct gggcacgtct ggaggaccaa gagcgtaagc tgattgatcg ggccgacatt   480
tcatcggtct acaccgtgac gggtccgctg tacgaacgtg atatgggcaa attaccgggt   540
acccaaaaag cacacacaat cccttcagcg tattggaaag tcatctttat taataactca   600
ccagcggtta atcactatgc tgcatttctc tttgatcaaa atacgccgaa aggggcagat   660
ttctgtcaat tcgcgtgac cgttgatgag atcgaaaagc ggactggcct cattatttgg   720
gccggcctgc cgcgtgacgt gcaggcctcc ctgaagagta accgggcgt tctgccggaa   780
ttaatgggct gtaagaac                                                 798
```

<210> SEQ ID NO 10
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Arg Phe Asn Asn Lys Met Leu Ala Leu Ala Ala Leu Leu Phe Ala
1               5                   10                  15

Ala Gln Ala Ser Ala Asp Thr Leu Glu Ser Ile Asp Asn Cys Ala Val
                20                  25                  30

Gly Cys Pro Thr Gly Gly Ser Ser Asn Val Ser Ile Val Arg His Ala
            35                  40                  45

Tyr Thr Leu Asn Asn Asn Ser Thr Thr Lys Phe Ala Asn Trp Val Ala
        50                  55                  60

Tyr His Ile Thr Lys Asp Thr Pro Ala Ser Gly Lys Thr Arg Asn Trp
65                  70                  75                  80

Lys Thr Asp Pro Ala Leu Asn Pro Ala Asp Thr Leu Ala Pro Ala Asp
                85                  90                  95

Tyr Thr Gly Ala Asn Ala Ala Leu Lys Val Asp Arg Gly His Gln Ala
            100                 105                 110

Pro Leu Ala Ser Leu Ala Gly Val Ser Asp Trp Glu Ser Leu Asn Tyr
        115                 120                 125

Leu Ser Asn Ile Thr Pro Gln Lys Ser Asp Leu Asn Gln Gly Ala Trp
    130                 135                 140

Ala Arg Leu Glu Asp Gln Glu Arg Lys Leu Ile Asp Arg Ala Asp Ile
145                 150                 155                 160

Ser Ser Val Tyr Thr Val Thr Gly Pro Leu Tyr Glu Arg Asp Met Gly
```

```
                    165                 170                 175
Lys Leu Pro Gly Thr Gln Lys Ala His Thr Ile Pro Ser Ala Tyr Trp
                180                 185                 190

Lys Val Ile Phe Ile Asn Asn Ser Pro Ala Val Asn His Tyr Ala Ala
            195                 200                 205

Phe Leu Phe Asp Gln Asn Thr Pro Lys Gly Ala Asp Phe Cys Gln Phe
        210                 215                 220

Arg Val Thr Val Asp Glu Ile Glu Lys Arg Thr Gly Leu Ile Ile Trp
225                 230                 235                 240

Ala Gly Leu Pro Arg Asp Val Gln Ala Ser Leu Lys Ser Lys Pro Gly
                245                 250                 255

Val Leu Pro Glu Leu Met Gly Cys Lys Asn
                260                 265

<210> SEQ ID NO 11
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgcgcttta acaacaagat gctggcgctg gccgctttac tgttcgcggc acaggcttcg       60
gcggacaccc tggaaagtat cgacaattgt gcggtcggtt gcccgactgg tggctcgagc      120
aatgtgtcga tcgttcgtca tgcttatacc cttaataata actcgaccac gaaattcgct      180
aactgggtag catatcacat tactaaggac actccggcca gcggtaagac gcgcaactgg      240
aagaccgatc cggcgctcaa tccggcagac accttagcac cggctgatta taccggtgca      300
aacgctgcgc tgaaggtgga tcgtggtcac caggcgccgt tggcatctct ggctggtgta      360
agcgactggg aaagccttaa ctatctcagc aacatcaccc cgcaaaagtc cgacctgaac      420
cagggagcct gggcagacct ggaggaccaa gagcgtaagc tgattcgtcg ggccgacatt      480
tcatcggtct acaccgtgac gggtccgctg tacgaacgtg atatgggcaa attaccgggt      540
acccaaaaag cacacacaat cccttcagcg tattggaaag tcatctttat taataactca      600
ccagcggtta atcactatgc tgcatttctc tttgatcaaa atacgccgaa aggggcagat      660
ttctgtcaat ttcgcgtgac cgttcgtgag atcgaaaagc ggactggcct cattatttgg      720
gccggcctgc cgcgtgacgt gcaggcctcc ctgaagagta accgggcgt tctgccggaa      780
ttaatgggct gtaagaac                                                   798

<210> SEQ ID NO 12
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Arg Phe Asn Asn Lys Met Leu Ala Leu Ala Ala Leu Leu Phe Ala
1               5                   10                  15

Ala Gln Ala Ser Ala Asp Thr Leu Glu Ser Ile Asp Asn Cys Ala Val
            20                  25                  30

Gly Cys Pro Thr Gly Gly Ser Ser Asn Val Ser Ile Val Arg His Ala
        35                  40                  45
```

-continued

```
Tyr Thr Leu Asn Asn Asn Ser Thr Thr Lys Phe Ala Asn Trp Val Ala
    50                  55                  60

Tyr His Ile Thr Lys Asp Thr Pro Ala Ser Gly Lys Thr Arg Asn Trp
65                  70                  75                  80

Lys Thr Asp Pro Ala Leu Asn Pro Ala Asp Thr Leu Ala Pro Ala Asp
                85                  90                  95

Tyr Thr Gly Ala Asn Ala Ala Leu Lys Val Asp Arg Gly His Gln Ala
            100                 105                 110

Pro Leu Ala Ser Leu Ala Gly Val Ser Asp Trp Glu Ser Leu Asn Tyr
        115                 120                 125

Leu Ser Asn Ile Thr Pro Gln Lys Ser Asp Leu Asn Gln Gly Ala Trp
    130                 135                 140

Ala Asp Leu Glu Asp Gln Glu Arg Lys Leu Ile Arg Arg Ala Asp Ile
145                 150                 155                 160

Ser Ser Val Tyr Thr Val Thr Gly Pro Leu Tyr Glu Arg Asp Met Gly
                165                 170                 175

Lys Leu Pro Gly Thr Gln Lys Ala His Thr Ile Pro Ser Ala Tyr Trp
            180                 185                 190

Lys Val Ile Phe Ile Asn Asn Ser Pro Ala Val Asn His Tyr Ala Ala
        195                 200                 205

Phe Leu Phe Asp Gln Asn Thr Pro Lys Gly Ala Asp Phe Cys Gln Phe
    210                 215                 220

Arg Val Thr Val Arg Glu Ile Glu Lys Arg Thr Gly Leu Ile Ile Trp
225                 230                 235                 240

Ala Gly Leu Pro Arg Asp Val Gln Ala Ser Leu Lys Ser Lys Pro Gly
                245                 250                 255

Val Leu Pro Glu Leu Met Gly Cys Lys Asn
            260                 265
```

THERMOLABILE SERRATIA MARCESCENS NUCLEASE

BACKGROUND

*Serratia Marcescens* Nuclease (EC 3.1.30.2) is a nonspecific nuclease, which digests all forms of DNA and RNA into one to four 5'-phosphorylated nucleotides. This enzyme has high specific activity, and each milligram of protein has 1 million units. It has been widely commercialized under different names, including Benzonase® by EMD Millipore Corp. (Burlington, Mass.), and for TurboNuclease™ by Accelagen (San Diego, Calif.). It is most widely used in purification following protein production.

Wild type *Serratia Marcescens* Nuclease is extremely thermostable, though it can be reversibly inactivated by adding EDTA, a high concentration of phosphate or a high concentration of salt. Irreversible complete heat inactivation can only be achieved by adding 100 mM NaOH, at 70° C. for 30 min. Under any of these inactivation conditions, it is very difficult for other reactions to continue in the solution.

A more thermolabile form of *Serratia Marcescens* Nuclease would make it more useful in certain applications after which the removal of the nuclease activity is needed.

SUMMARY

The invention relates to an engineered thermolabile mutant of *Serratia Marcescens* Nuclease. In the same buffer as used for optimal enzyme activity, after 60° C. for 20 min, while the wild type retained 12.5% activity, a thermolabile mutant R146D/D156R/D229R/D245R (SEQ ID NO: 12, without the 21 amino acid N-terminal signal peptide) of *Serratia Marcescens* Nuclease retained only 0.39% activity. Thus, it is 32 fold more thermolabile than the wild type. Nevertheless, heat inactivation is dependent on temperature, time course and buffer composition. Through increased temperature applied for a longer time under suitable buffer conditions, an more complete heat inactivation of the thermolabile mutant R146D/D156R/D229R/D245R could be achieved—but other desired reactions could be affected. The degree of required inactivation can be balanced against the inhibition of other desired reactions, in determining the temperature and time of exposure for the solution under consideration. These conditions can be determined by routine experimentation.

BRIEF DESCRIPTION OF THE FIGURES

FIG. 1 is a gel showing the thermostability comparison of wild type *Serratia Marcescens* Nuclease and mutant R146D/D156R/D229R/D245R; Panel A: WT *Serratia Marcescens* Nuclease unheated; Panel B: WT *Serratia Marcescens* Nuclease after 60° C. for 20 min; Panel C: mutant R146D/D156R/D229R/D245R unheated; Panel D: mutant R146D/D156R/D229R/D245R after 60° C. for 20 min. Lane M: 1 kb DNA ladder (New England Biolabs, Inc.); Lane 1 to 24, *Serratia Marcescens* Nuclease in 2 fold serial dilution with 10 mM Tris-HCl, pH8.0.

DETAILED DESCRIPTION

"R146D/D156R/D229R/D245R" and "mutant R146D/D156R/D229R/D245R" refers to a mutant *Serratia Marcescens* Nuclease with mutations at the four sites in the name, as shown in SEQ ID NO: 12 (but without the first 21 amino acids from the N-terminus, which are a signal peptide, cleaved off during expression).

The term "conservative variant" includes modifications of given sequences that result in conserved function. For example, in the context of nucleic acids, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid.

Similarly, "conservative variants" of a peptide sequence are expected to retain function. For example, Guo, "Protein Tolerance to Random Amino Acid Change" (PNAS 101: 9205-10; 2004), demonstrates that one of skill can modify peptides successfully even "without detailed knowledge of the ways in which a protein's structure relates to its functional usefulness . . . " A conservative amino acid substitution refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) supra). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

Conservative variants of the mutant R146D/D156R/D229R/D245R can be made in accordance with well known methods, including those described below for producing R146D/D156R/D229R/D245R or other *Serratia Marcescens* Nuclease mutants.

EXAMPLES

*Serratia Marcescens* Nuclease was expressed extracellularly in C2566 (New England Biolabs, MA) with the plasmid construct formed with a kanamycin resistant pBAD vector. When expressed, the first 21 amino acids are removed from the mature protein. The mutation amino acid residue numbering is from the first amino acid from the signal peptide. The following point mutations were made individually, and some in combinations, as described in the Sequences section, using inverse PCR, to amplify DNA with only the desired mutant sequence: D22R, E25K, D28R, R46D, K58E, K69E, D70R, K76E, R78D, K81E, D83R, D90R, D96R, K105E, D107R, R108D, D122R, E124K, K136E, D138R, R146D (SEQ ID NO: 4), E148K, D149R, E151K, R152D, K153E, D156R (SEQ ID NO: 6), R157D, D159R, E172K, R173D, D174R, K177E, K183E, K193E, D212R, K217E, D220R, R225D, D229R (SEQ ID NO: 8), E230K, E232K, K233E, R234D, D245R (SEQ ID NO: 10), D246R, K252E and K254E.

The mutant R146D/D156R/D229R/D245R and other mutants can be generated using mutagenesis PCR, to produce an amplified mutated DNA oligomer. The oligomer can then be translated into a protein (the nuclease) in a production system, e.g., *E. Coli*. See U.S. Pat. Nos. 4,873,192 & 5,556,747 (both incorporated by reference) regarding processes relating to site-directed mutagenesis.

*Serratia Marcescens* Nuclease activity was assayed with culture media against lambda DNA. Lambda DNA is digested into a smear first, then to 1 to 4 nucleotides. Culture media was added to make a final concentration of 10 mM Tris-HCl, 2 mM $MgCl_2$, pH8.0.

A thermo-stability assay was performed comparing enzyme activity before and after incubation at 60° C. for 20 minutes. The reaction condition were: 2 μl culture media containing *Serratia Marcescens* Nuclease, 2 μl of 10× reaction buffer, final concentration was 10 mM pH 8.0, 2 mM $MgCl_2$, 0.4 μl 500 ng/ul Lambda DNA, 15.6 μl $H_2O$. The reaction was at 37° C. for one hour. DNA is run on 1% agarose gel. Four mutants, R146D, D156R, D229R and D245R, showed more heat inactivation than the wild type. A mutant containing all four selected mutations, mutant R146D/D156R/D229R/D245R, was most thermolabile. Comparison of the activity before and after heating is shown as FIG. 1. In comparing the DNA running pattern from different panels, it is noted that Panel A 15-17 is close to Panel B 12-14, meaning that heating to 60° C. for 20 min reduces the WT enzyme activity to ⅛, or 12.5%. Panel C 15-17 is close to Panel 7-9, meaning that heating to 60° C. for 20 min reduces the R146D/D156R/D229R/D245R mutant's enzyme activity to 1/256, or 0.39%.

Thus, in the same buffer which generated optimal enzyme activity, at 60° C. for 20 min, the Wild type *Serratia Marcescens* Nuclease retained 12.5% activity whereas mutant R146D/D156R/D229R/D245R only retained 0.39% activity.

Using the Mutant R146D/D156R/D229R/D245R

The uses for the mutant R146D/D156R/D229R/D245R include removing DNA, and protein purification and sample preparation from biopharmaceutical reaction products, similar to uses described for Benzonase® by EMD Millipore Corp. (Burlington, Mass.), and for TurboNuclease™ by Accelagen (San Diego, Calif.), including but not limited to the following: viral vaccine production; viral like particle production; viral vector production for vaccine and cell and gene therapy applications; prevention of cell clumping; viscosity reduction; FAB purification; and, protein and inclusion body purification. The degree of degradation by the mutant R146D/D156R/D229R/D245R can be controlled to avoid unwanted product digestion by elevating the temperature after a length of time sufficient to degrade most contaminant DNA oligonucleotides in a mixture; but before there is significant unwanted degradation. The reaction stop time can be determined by routine experimentation, based on the knowledge that heating to 60° C. for 20 min reduces the R146D/D156R/D229R/D245R mutant's enzyme activity to 1/256, or 0.39%; meaning there may be such lag between heating and effectively stopping enzyme activity.

Sequences

DNA sequence of *Serratia Marcescens* Nuclease WT (SEQ ID NO: 1):

```
ATGCGCTTTA ACAACAAGAT GCTGGCGCTG GCCGCTTTAC TGTTCGCGGC ACAGGCTTCG   60

GCGGACACCC TGGAAAGTAT CGACAATTGT GCGGTCGGTT GCCCGACTGG TGGCTCGAGC  120

AATGTGTCGA TCGTTCGTCA TGCTTATACC CTTAATAATA ACTCGACCAC GAAATTCGCT  180

AACTGGGTAG CATATCACAT TACTAAGGAC ACTCCGGCCA GCGGTAAGAC GCGCAACTGG  240

AAGACCGATC CGGCGCTCAA TCCGGCAGAC ACCTTAGCAC CGGCTGATTA TACCGGTGCA  300

AACGCTGCGC TGAAGGTGGA TCGTGGTCAC CAGGCGCCGT TGGCATCTCT GGCTGGTGTA  360

AGCGACTGGG AAAGCCTTAA CTATCTCAGC AACATCACCC CGCAAAAGTC CGACCTGAAC  420

CAGGGAGCCT GGGCACGTCT GGAGGACCAA GAGCGTAAGC TGATTGATCG GGCCGACATT  480

TCATCGGTCT ACACCGTGAC GGGTCCGCTG TACGAACGTG ATATGGGCAA ATTACCGGGT  540

ACCCAAAAAG CACACACAAT CCCTTCAGCG TATTGGAAAG TCATCTTTAT TAATAACTCA  600

CCAGCGGTTA ATCACTATGC TGCATTTCTC TTTGATCAAA ATACGCCGAA AGGGGCAGAT  660

TTCTGTCAAT TTCGCGTGAC CGTTGATGAG ATCGAAAAGC GGACTGGCCT CATTATTTGG  720
```

```
GCCGGCCTGC CGGATGACGT GCAGGCCTCC CTGAAGAGTA AACCGGGCGT TCTGCCGGAA 780

TTAATGGGCT GTAAGAAC
```

Protein sequence of *Serratia Marcescens* Nuclease WT (SEQ ID NO: 2). The underlined portion (first 21 amino acids from the N-terminus) is a signal peptide which is cleaved off during expression.

```
MRFNNKMLALAALLFAAQASADTLESIDNCAVGCPTGGSSNVSIVRHAYTLNNNSTTKFA   60

NWVAYHITKDTPASGKTRNWKTDPALNPADTLAPADYTGANAALKVDRGHQAPLASLAGV  120

SDWESLNYLSNITPQKSDLNQGAWARLEDQERKLIDRADISSVYTVTGPLYERDMGKLPG  180

TQKAHTIPSAYWKVIFINNSPAVNHYAAFLFDQNTPKGADFCQFRVTVDEIEKRTGLIIW  240

AGLPDDVQASLKSKPGVLPELMGCKN  266
```

DNA sequence of *Serratia Marcescens* Nuclease R146D (SEQ ID NO: 3):

```
ATGCGCTTTA ACAACAAGAT GCTGGCGCTG GCCGCTTTAC TGTTCGCGGC ACAGGCTTCG   60

GCGGACACCC TGGAAAGTAT CGACAATTGT GCGGTCGGTT GCCCGACTGG TGGCTCGAGC  120

AATGTGTCGA TCGTTCGTCA TGCTTATACC CTTAATAATA ACTCGACCAC GAAATTCGCT  180

AACTGGGTAG CATATCACAT TACTAAGGAC ACTCCGGCCA GCGGTAAGAC GCGCAACTGG  240

AAGACCGATC CGGCGCTCAA TCCGGCAGAC ACCTTAGCAC CGGCTGATTA TACCGGTGCA  300

AACGCTGCGC TGAAGGTGGA TCGTGGTCAC CAGGCGCCGT TGGCATCTCT GGCTGGTGTA  360

AGCGACTGGG AAAGCCTTAA CTATCTCAGC AACATCACCC CGCAAAAGTC CGACCTGAAC  420

CAGGGAGCCT GGGCAGACCT GGAGGACCAA GAGCGTAAGC TGATTGATCG GGCCGACATT  480

TCATCGGTCT ACACCGTGAC GGGTCCGCTG TACGAACGTG ATATGGGCAA ATTACCGGGT  540

ACCCAAAAAG CACACACAAT CCCTTCAGCG TATTGGAAAG TCATCTTTAT TAATAACTCA  600

CCAGCGGTTA ATCACTATGC TGCATTTCTC TTTGATCAAA ATACGCCGAA AGGGGCAGAT  660

TTCTGTCAAT TTCGCGTGAC CGTTGATGAG ATCGAAAAGC GGACTGGCCT CATTATTTGG  720

GCCGGCCTGC CGGATGACGT GCAGGCCTCC CTGAAGAGTA AACCGGGCGT TCTGCCGGAA  780

TTAATGGGCT GTAAGAAC
```

Protein sequence of *Serratia Marcescens* Nuclease R146D (SEQ ID NO: 4). The underlined portion (first 21 amino acids from the N-terminus) is a signal peptide which is cleaved off during expression:

```
MRFNNKMLALAALLFAAQASADTLESIDNCAVGCPTGGSSNVSIVRHAYTLNNNSTTKFA   60

NWVAYHITKDTPASGKTRNWKTDPALNPADTLAPADYTGANAALKVDRGHQAPLASLAGV  120

SDWESLNYLSNITPQKSDLNQGAWADLEDQERKLIDRADISSVYTVTGPLYERDMGKLPG  180

TQKAHTIPSAYWKVIFINNSPAVNHYAAFLFDQNTPKGADFCQFRVTVDEIEKRTGLIIW  240

AGLPDDVQASLKSKPGVLPELMGCKN  266
```

DNA sequence of *Serratia Marcescens* Nuclease D156R (SEQ ID NO: 5):

```
ATGCGCTTTA ACAACAAGAT GCTGGCGCTG GCCGCTTTAC TGTTCGCGGC ACAGGCTTCG  60
GCGGACACCC TGGAAAGTAT CGACAATTGT GCGGTCGGTT GCCCGACTGG TGGCTCGAGC 120
AATGTGTCGA TCGTTCGTCA TGCTTATACC CTTAATAATA ACTCGACCAC GAAATTCGCT 180
AACTGGGTAG CATATCACAT TACTAAGGAC ACTCCGGCCA GCGGTAAGAC GCGCAACTGG 240
AAGACCGATC CGGCGCTCAA TCCGGCAGAC ACCTTAGCAC CGGCTGATTA TACCGGTGCA 300
AACGCTGCGC TGAAGGTGGA TCGTGGTCAC CAGGCGCCGT TGGCATCTCT GGCTGGTGTA 360
AGCGACTGGG AAAGCCTTAA CTATCTCAGC AACATCACCC CGCAAAAGTC CGACCTGAAC 420
CAGGGAGCCT GGGCACGTCT GGAGGACCAA GAGCGTAAGC TGATTCGTCG GGCCGACATT 480
TCATCGGTCT ACACCGTGAC GGGTCCGCTG TACGAACGTG ATATGGGCAA ATTACCGGGT 540
ACCCAAAAAG CACACACAAT CCCTTCAGCG TATTGGAAAG TCATCTTTAT TAATAACTCA 600
CCAGCGGTTA ATCACTATGC TGCATTTCTC TTTGATCAAA ATACGCCGAA AGGGGCAGAT 660
TTCTGTCAAT TTCGCGTGAC CGTTGATGAG ATCGAAAAGC GGACTGGCCT CATTATTTGG 720
GCCGGCCTGC CGGATGACGT GCAGGCCTCC CTGAAGAGTA AACCGGGCGT TCTGCCGGAA 780
TTAATGGGCT GTAAGAAC
```

Protein sequence of *Serratia Marcescens* Nuclease D156R (SEQ ID NO: 6). The underlined portion (first 21 amino acids from the N-terminus) is a signal peptide which is cleaved off during expression:

```
MRFNNKMLALAALLFAAQASADTLESIDNCAVGCPTGGSSNVSIVRHAYTLNNNSTTKFA  60
NWVAYHITKDTPASGKTRNWKTDPALNPADTLAPADYTGANAALKVDRGHQAPLASLAGV 120
SDWESLNYLSNITPQKSDLNQGAWARLEDQERKLIRRADISSVYTVTGPLYERDMGKLPG 180
TQKAHTIPSAYWKVIFINNSPAVNHYAAFLFDQNTPKGADFCQFRVTVDEIEKRTGLIIW 240
AGLPDDVQASLKSKPGVLPELMGCKN 266
```

DNA sequence of *Serratia Marcescens* Nuclease D229R (SEQ ID NO: 7):

```
ATGCGCTTTA ACAACAAGAT GCTGGCGCTG GCCGCTTTAC TGTTCGCGGC ACAGGCTTCG  60
GCGGACACCC TGGAAAGTAT CGACAATTGT GCGGTCGGTT GCCCGACTGG TGGCTCGAGC 120
AATGTGTCGA TCGTTCGTCA TGCTTATACC CTTAATAATA ACTCGACCAC GAAATTCGCT 180
AACTGGGTAG CATATCACAT TACTAAGGAC ACTCCGGCCA GCGGTAAGAC GCGCAACTGG 240
AAGACCGATC CGGCGCTCAA TCCGGCAGAC ACCTTAGCAC CGGCTGATTA TACCGGTGCA 300
AACGCTGCGC TGAAGGTGGA TCGTGGTCAC CAGGCGCCGT TGGCATCTCT GGCTGGTGTA 360
AGCGACTGGG AAAGCCTTAA CTATCTCAGC AACATCACCC CGCAAAAGTC CGACCTGAAC 420
CAGGGAGCCT GGGCACGTCT GGAGGACCAA GAGCGTAAGC TGATTGATCG GGCCGACATT 480
TCATCGGTCT ACACCGTGAC GGGTCCGCTG TACGAACGTG ATATGGGCAA ATTACCGGGT 540
ACCCAAAAAG CACACACAAT CCCTTCAGCG TATTGGAAAG TCATCTTTAT TAATAACTCA 600
CCAGCGGTTA ATCACTATGC TGCATTTCTC TTTGATCAAA ATACGCCGAA AGGGGCAGAT 660
TTCTGTCAAT TTCGCGTGAC CGTTCGTGAG ATCGAAAAGC GGACTGGCCT CATTATTTGG 720
GCCGGCCTGC CGGATGACGT GCAGGCCTCC CTGAAGAGTA AACCGGGCGT TCTGCCGGAA 780
TTAATGGGCT GTAAGAAC
```

Protein sequence of *Serratia Marcescens* Nuclease D229R (SEQ ID NO: 8). The underlined portion (first 21 amino acids from the N-terminus) is a signal peptide which is cleaved off during expression:

MRFNNKMLALAALLFAAQASADTLESIDNCAVGCPTGGSSNVSIVRHAYTLNNNSTTKFA 60

NWVAYHITKDTPASGKTRNWKTDPALNPADTLAPADYTGANAALKVDRGHQAPLASLAGV 120

SDWESLNYLSNITPQKSDLNQGAWARLEDQERKLIDRADISSVYTVTGPLYERDMGKLPG 180

TQKAHTIPSAYWKVIFINNSPAVNHYAAFLFDQNTPKGADFCQFRVTVREIEKRTGLIIW 240

AGLPDDVQASLKSKPGVLPELMGCKN 266

DNA sequence of *Serratia Marcescens* Nuclease D245R (SEQ ID NO: 9):

ATGCGCTTTA ACAACAAGAT GCTGGCGCTG GCCGCTTTAC TGTTCGCGGC ACAGGCTTCG 60

GCGGACACCC TGGAAAGTAT CGACAATTGT GCGGTCGGTT GCCCGACTGG TGGCTCGAGC 120

AATGTGTCGA TCGTTCGTCA TGCTTATACC CTTAATAATA ACTCGACCAC GAAATTCGCT 180

AACTGGGTAG CATATCACAT TACTAAGGAC ACTCCGGCCA GCGGTAAGAC GCGCAACTGG 240

AAGACCGATC CGGCGCTCAA TCCGGCAGAC ACCTTAGCAC CGGCTGATTA TACCGGTGCA 300

AACGCTGCGC TGAAGGTGGA TCGTGGTCAC CAGGCGCCGT TGGCATCTCT GGCTGGTGTA 360

AGCGACTGGG AAAGCCTTAA CTATCTCAGC AACATCACCC CGCAAAAGTC CGACCTGAAC 420

CAGGGAGCCT GGGCACGTCT GGAGGACCAA GAGCGTAAGC TGATTGATCG GGCCGACATT 480

TCATCGGTCT ACACCGTGAC GGGTCCGCTG TACGAACGTG ATATGGGCAA ATTACCGGGT 540

ACCCAAAAAG CACACACAAT CCCTTCAGCG TATTGGAAAG TCATCTTTAT TAATAACTCA 600

CCAGCGGTTA ATCACTATGC TGCATTTCTC TTTGATCAAA ATACGCCGAA AGGGGCAGAT 660

TTCTGTCAAT TTCGCGTGAC CGTTGATGAG ATCGAAAAGC GGACTGGCCT CATTATTTGG 720

GCCGGCCTGC CGCGTGACGT GCAGGCCTCC CTGAAGAGTA AACCGGGCGT TCTGCCGGAA 780

TTAATGGGCT GTAAGAAC

Protein sequence of *Serratia Marcescens* Nuclease D245R (SEQ ID NO: 10). The underlined portion (first 21 amino acids from the N-terminus) is a signal peptide which is cleaved off during expression:

MRFNNKMLALAALLFAAQASADTLESIDNCAVGCPTGGSSNVSIVRHAYTLNNNSTTKFA 60

NWVAYHITKDTPASGKTRNWKTDPALNPADTLAPADYTGANAALKVDRGHQAPLASLAGV 120

SDWESLNYLSNITPQKSDLNQGAWARLEDQERKLIDRADISSVYTVTGPLYERDMGKLPG 180

TQKAHTIPSAYWKVIFINNSPAVNHYAAFLFDQNTPKGADFCQFRVTVDEIEKRTGLIIW 240

AGLPRDVQASLKSKPGVLPELMGCKN 266

DNA sequence of *Serratia Marcescens* Nuclease R146D/D156R/D229R/D245R (SEQ ID NO: 11):

ATGCGCTTTA ACAACAAGAT GCTGGCGCTG GCCGCTTTAC TGTTCGCGGC ACAGGCTTCG 60

GCGGACACCC TGGAAAGTAT CGACAATTGT GCGGTCGGTT GCCCGACTGG TGGCTCGAGC 120

AATGTGTCGA TCGTTCGTCA TGCTTATACC CTTAATAATA ACTCGACCAC GAAATTCGCT 180

AACTGGGTAG CATATCACAT TACTAAGGAC ACTCCGGCCA GCGGTAAGAC GCGCAACTGG 240

AAGACCGATC CGGCGCTCAA TCCGGCAGAC ACCTTAGCAC CGGCTGATTA TACCGGTGCA 300

```
AACGCTGCGC TGAAGGTGGA TCGTGGTCAC CAGGCGCCGT TGGCATCTCT GGCTGGTGTA    360

AGCGACTGGG AAAGCCTTAA CTATCTCAGC AACATCACCC CGCAAAAGTC CGACCTGAAC    420

CAGGGAGCCT GGGCAGACCT GGAGGACCAA GAGCGTAAGC TGATTCGTCG GGCCGACATT    480

TCATCGGTCT ACACCGTGAC GGGTCCGCTG TACGAACGTG ATATGGGCAA ATTACCGGGT    540

ACCCAAAAAG CACACACAAT CCCTTCAGCG TATTGGAAAG TCATCTTTAT TAATAACTCA    600

CCAGCGGTTA ATCACTATGC TGCATTTCTC TTTGATCAAA ATACGCCGAA AGGGGCAGAT    660

TTCTGTCAAT TTCGCGTGAC CGTTCGTGAG ATCGAAAAGC GGACTGGCCT CATTATTTGG    720

GCCGGCCTGC CGCGTGACGT GCAGGCCTCC CTGAAGAGTA AACCGGGCGT TCTGCCGGAA    780

TTAATGGGCT GTAAGAAC
```

Protein sequence of *Serratia Marcescens* Nuclease R146D/D156R/D229R/D245R (SEQ ID NO: 12). The underlined portion (first 21 amino acids from the N-terminus) is a signal peptide which is cleaved off during expression:

```
MRFNNKMLALAALLFAAQAS ADTLESIDNCAVGCPTGGSSNVSIVRHAYTLNNNSTTKFA     60

NWVAYHITKDTPASGKTRNWKTDPALNPADTLAPADYTGANAALKVDRGHQAPLASLAGV    120

SDWESLNYLSNITPQKSDLNQGAWADLEDQERKLIRRADISSVYTVTGPLYERDMGKLPG    180

TQKAHTIPSAYWKVIFINNSPAVNHYAAFLFDQNTPKGADFCQFRVTVREIEKRTGLIIW    240

AGLPRDVQASLKSKPGVLPELMGCKN    266
```

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A thermolabile *Serratia Marcescens* Nuclease mutant, comprising: the amino acid sequence of SEQ ID NO: 12 not including the first 21 amino acids from the N-terminus.

2. A DNA sequence encoding the amino acid sequence of SEQ ID NO: 12 not including the first 21 amino acids from the N-terminus.

3. The DNA sequence of SEQ ID NO: 11.

4. A method of removing nucleic acids from a solution following protein production in said solution, comprising:

adding to the solution, after protein production, a thermolabile *Serratia Marcescens* Nuclease mutant having the amino acid sequence of SEQ ID NO: 12 not including the first 21 amino acids from the N-terminus, under conditions and times to permit the thermolabile *Serratia Marcescens* Nuclease mutant to degrade nucleic acid in the solution; and terminating the *Serratia Marcescens* Nuclease mutant activity after a period sufficient to degrade nucleic acid in the solution, by heating the solution.

5. The method of claim 4 wherein said nucleic acid are DNA oligomers.

* * * * *